United States Patent [19]

Schumann

[11] Patent Number: Plant 5,371

[45] Date of Patent: Dec. 18, 1984

[54] GERANIUM PLANT NAMED POLKA

[75] Inventor: Ingeborg Schumann, Bad Ems, Fed. Rep. of Germany

[73] Assignee: Pelargonien-Fischer KG, Hillscheid, Fed. Rep. of Germany

[21] Appl. No.: 547,896

[22] Filed: Nov. 2, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of geranium plant particularly characterized by the combined features of carmine red flower color, double flower form, large flowerhead, tolerance to low temperatures, fast rooting, good branching, and early response.

3 Drawing Figures

The present invention comprises a new and distinct cultivar of geranium, botanically known as *Pelargonium zonale,* and hereinafter referred to by the cultivar name Polka.

Polka is a product of planned breeding program which had the objective of creating new geranium cultivars with a novel carmine red flower color, semi-double flower form, compact habit, tolerance of low cultivation temperatures, fast rooting, and good quality of chlorophyll for transportation.

Polka was originated from a hybridization made in a controlled breeding program in Hillscheid, Federal Republic of Germany in 1979. The new cultivar resulted from the self-breeding of the unpatented cultivar Purlapen.

Polka was discovered and selected as one flowering plant within the progeny of the stated cross by Ingeborg Schumann on June 27, 1980 in a controlled environment in Hillscheid, Federal Republic of Germany.

The first act of asexual reproduction of Polka was accomplished when vegetative cuttings were taken from the initial selection in January, 1981 in a controlled environment in Hillscheid, Federal Republic of Germany by a technician working under formulations established and supervised by Ingeborg Schumann. Horticultural examination of selected units initiated in the Spring of 1981 and continued in 1982 has demonstrated that the combination of characteristics as herein disclosed for Polka are firmly fixed and are retained through successive generations of asexual reproduction.

Polka has not been observed under all possible environmental conditions. The phenotype may vary significantly with variations in environment such as temperature, light intensity, and day length. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Polka which in combination distinguish this geranium as a new and distinct cultivar:

1. Carmine red flower color.
2. Double flower form.
3. Low temperature tolerance, with cultivation below 12° C. being possible.
4. Large flowerhead.
5. Compact habit.

6. Good chlorophyll quality for transport.
7. Fast rooting.
8. Good branching, producing an average of 3.7 branches per plant.
9. Early response.

Of the many commercial cultivars known to the present inventor, the most similar in comparison to Polka is the parent cultivar Purlapen. Reference is made to attached Chart A which compares certain characteristics of Polka to those same characteristics of Purlapen. Polka has a more intense red flower color, a larger corolla and umbel, and a somewhat earlier flowering response.

The accompanying photographic drawings show typical flower and foliage characteristics of Polka, with colors being as true as possible with illustrations of this type. Sheet 1 is a color photograph of a potted plant of Polka. Sheet 2 is a relatively enlarged color photograph of the flowers, buds and foliage, and sheet 3 is a black and white print of the underside of typical foliage of Polka.

In the following description color references are made to The Royal Horticultural Society Colour Chart, and to The Horticultural Color Chart (H.C.C.). The color values were determined between 2:20 and 2:35 P.M. on Aug. 11, 1983 under 25,000 Klux at Hillscheid, Federal Republic of Germany.

CLASSIFICATION

Botanical: A hybrid of the genus *Pelargonium* 'Hert.
Commercial: Polka.

INFLORESCENCE

Umbel:

*Average diameter.*—119 mm.
*Average depth.*—87 mm.
*Peduncle length.*—230 mm.
*Pedicel length.*—28 mm. (With anthocyan).

Corolla:

*Average diameter.*—50 mm.
*Form.*—Double, not round.
*Color (general tonality from a distance of three meter).*—R.H.S. 46C, H.C.C. 721/2.
*Color (abaxial).*—R.H.S. 46C, H.C.C. 721/2.
*Color (adaxial).*—H.C.C. 721/3.

Bud:

*Shape.*—Elliptic to round.

*Color (abaxial).*—Light red.

Reproductive organs:

*Androecium.*—Monodelphous; 6–7 stamens; moderate to scant pollen.

*Gynoecium.*—5–6 Lobed stigma, sometimes deformed; style, color red.

Spring flowering response period:

In Hillscheid, Federal Republic of Germany in 1982, 75% of plants with at least 1 flower opened 13 weeks after planting of unrooted cuttings.

Outdoor flower production:

The flower count in 1982 in Hillscheid, Federal Republic of Germany was between 52 and 56 flowers per plant for June through October observation period.

Durability: Shatter resistance good.

PLANT

Foliage:

*Form.*—Kidney shaped.

*Margin.*—Bicrenate.

*Color (abaxial).*—Medium green.

*Color (zonation).*—Brown, medium zonation.

*Tolerance to botrytis.*—Good.

General appearance and form:

*Internode length.*—32 mm.

*Branching pattern.*—3.7.

*Height.*—290 mm.

CHART A

| | Corolla Color | Branching Habit (number of branches) | Zonation | Umbel Diameter |
|---|---|---|---|---|
| Purlapen | HCC 22 RHS 57A | 3.5 | no | 101 mm |
| Polka | HCC 721/2 | 3.7 | middle | 119 mm |

| | Depth | Corolla Diameter | Spring Flowering Response | Outdoor Flower Production |
|---|---|---|---|---|
| Purlapen | 70 mm | 45 mm | 70% | 57–60 |
| Polka | 87 mm | 50 mm | 75% | 52–56 |

I claim:

1. A new and distinct cultivar of geranium plant named Polka, as described and illustrated, and particularly characterized by the combined features of carmine red flower color, double flower form, large flowerhead, tolerance to low temperatures, fast rooting, good branching, and early response.

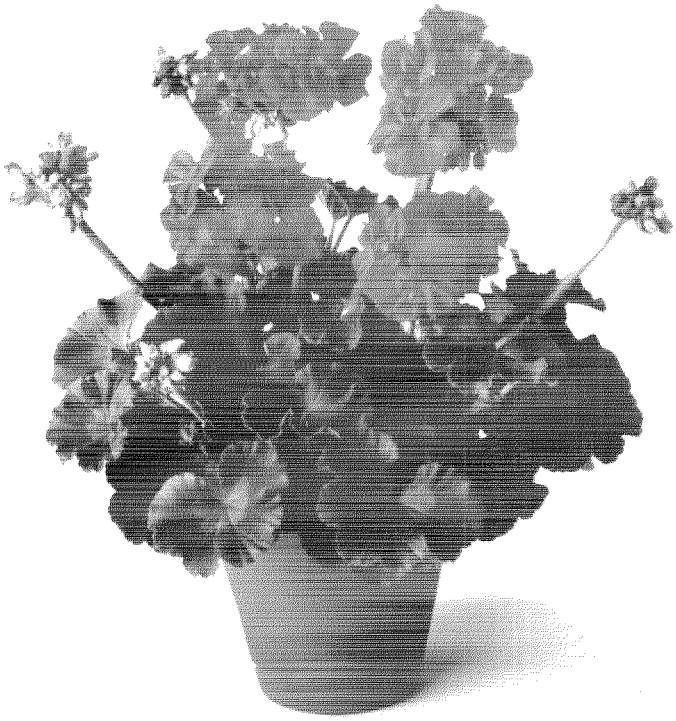

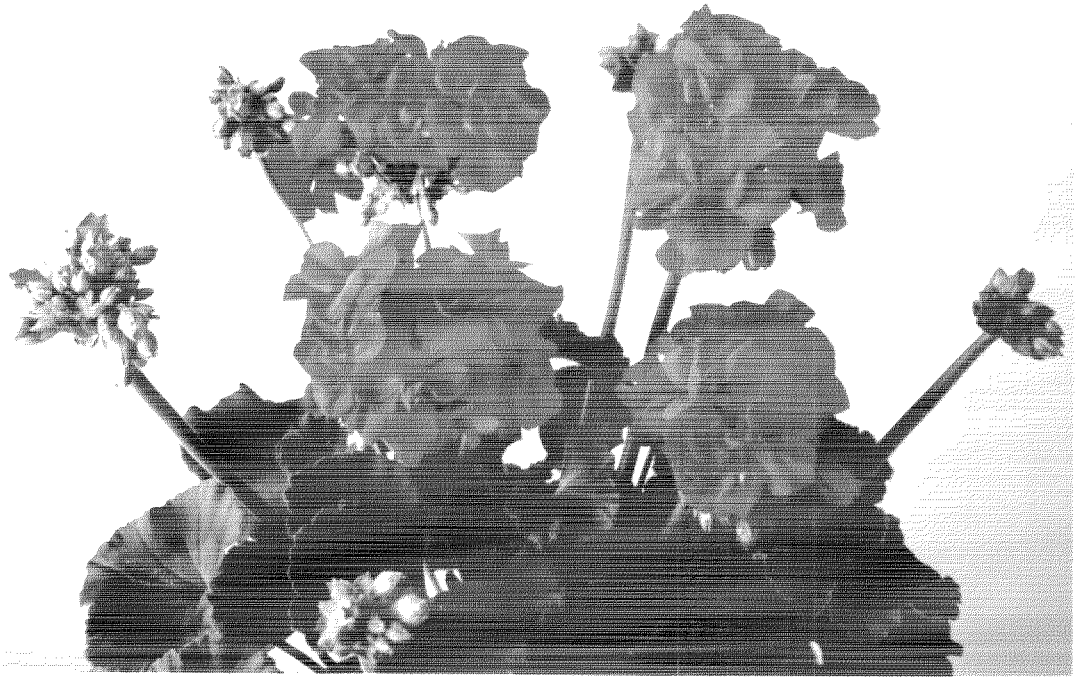

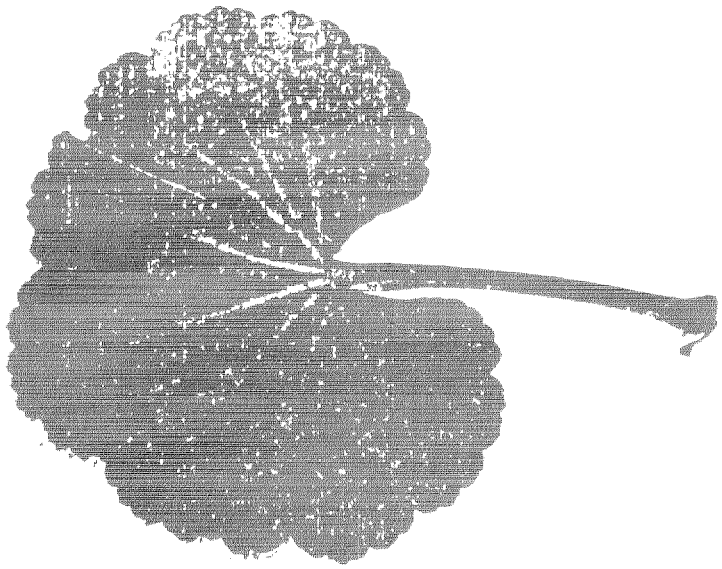
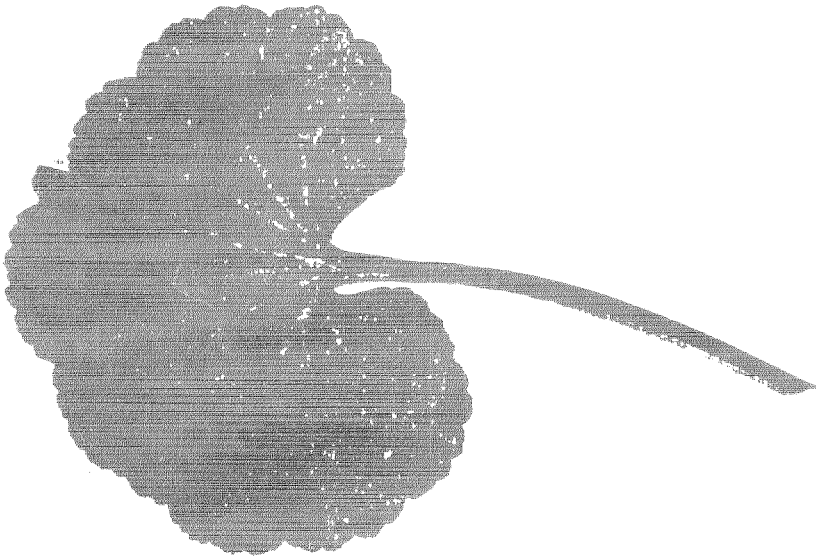

* * * * *